US012672809B2

(12) United States Patent
Chen

(10) Patent No.: US 12,672,809 B2
(45) Date of Patent: Jul. 7, 2026

(54) DEVICE FOR MONITORING HEAT STRESS

(71) Applicant: Zhibo Chen, New Territories (HK)

(72) Inventor: Zhibo Chen, New Territories (HK)

( * ) Notice: Subject to any disclaimer, the term of this patent is extended or adjusted under 35 U.S.C. 154(b) by 293 days.

(21) Appl. No.: 18/262,058

(22) PCT Filed: Jan. 21, 2021

(86) PCT No.: PCT/IB2021/050444
§ 371 (c)(1),
(2) Date: Jul. 19, 2023

(87) PCT Pub. No.: WO2022/157542
PCT Pub. Date: Jul. 28, 2022

(65) Prior Publication Data
US 2024/0293060 A1 Sep. 5, 2024

(51) Int. Cl.
*A61B 5/16* (2006.01)
*A61B 5/00* (2006.01)
(Continued)

(52) U.S. Cl.
CPC .......... *A61B 5/165* (2013.01); *A61B 5/02055* (2013.01); *A61B 5/14517* (2013.01); *A61B 5/14546* (2013.01); *A61B 5/681* (2013.01); *A61B 5/7267* (2013.01); *A61B 5/7275* (2013.01); *A61B 5/746* (2013.01); *A61B 5/02438* (2013.01); *A61B 2562/04* (2013.01); *A61B 2562/06* (2013.01); *A61B 2562/164* (2013.01)

(58) Field of Classification Search
CPC . A61B 5/165; A61B 5/02055; A61B 5/14517;

A61B 5/14546; A61B 5/681; A61B 5/7267; A61B 5/7275; A61B 5/746; A61B 5/02438; A61B 2562/04; A61B 2562/06; A61B 2562/164; A61B 5/024; A61B 5/6802; A61B 2560/0242; A61B 5/01; G16H 50/20; G16H 50/30
See application file for complete search history.

(56) References Cited

U.S. PATENT DOCUMENTS 10,485,475 B1 * 11/2019 Miller .................. A61B 5/4875
10,617,359 B2 * 4/2020 Saito ..................... A61B 5/1112
(Continued)

FOREIGN PATENT DOCUMENTS

CN     204520692 U     8/2015
CN     206421048 U     8/2017
(Continued)

*Primary Examiner* — Michael J Lau
(74) *Attorney, Agent, or Firm* — Hinckley Allen & Snyder; Stephen Holmes

(57) ABSTRACT

A wearable heat stress monitor (100) comprising: a first sensor (110), the first sensor (110) comprising an electrode (115) for sensing a sweat parameter (110A) and at least one further sensor (120) for sensing a body parameter or an environmental parameter (120A). The heat stress monitor (100) further comprises a processor (130) to determine a heat stress level based on the sweat parameter (110A) sensed by the first sensor (110) and the body parameter or environmental parameter (120A) sensed by the at least one further sensor (120) and an output module (140) for outputting information based on the heat stress level determined by the processor (130).

18 Claims, 11 Drawing Sheets

(51) Int. Cl.
    *A61B 5/0205*          (2006.01)
    *A61B 5/145*           (2006.01)
    *A61B 5/024*           (2006.01)

(56)             References Cited

U.S. PATENT DOCUMENTS

| | | | |
|---|---|---|---|
| 11,504,040 B2* | 11/2022 | Zhang | A61B 5/256 |
| 2002/0017997 A1* | 2/2002 | Felkowitz | G01K 1/024 |
| | | | 374/E1.004 |
| 2009/0198112 A1* | 8/2009 | Park | A61B 5/02438 |
| | | | 600/301 |
| 2010/0312142 A1* | 12/2010 | Demirdjian | B60N 2/0023 |
| | | | 600/587 |
| 2011/0022332 A1* | 1/2011 | Kailas | A61B 5/165 |
| | | | 702/42 |
| 2011/0245689 A1* | 10/2011 | Suzuki | A61B 5/024 |
| | | | 600/483 |
| 2014/0018641 A1* | 1/2014 | Yoshino | A61B 5/7275 |
| | | | 600/301 |
| 2014/0221792 A1* | 8/2014 | Miller | A61B 5/4875 |
| | | | 600/595 |
| 2016/0178392 A1* | 6/2016 | Goldfain | G01C 22/006 |
| | | | 702/158 |
| 2017/0143230 A1* | 5/2017 | Yamaji | A61F 13/42 |
| 2019/0117170 A1* | 4/2019 | Begtrup | A61B 5/0533 |
| 2019/0175104 A1* | 6/2019 | Malik | A61B 5/145 |
| 2020/0352456 A1* | 11/2020 | Joseph | A61B 5/486 |
| 2021/0004695 A1* | 1/2021 | Ike | G16H 50/20 |
| 2021/0068736 A1* | 3/2021 | Grahm | G16H 40/63 |

FOREIGN PATENT DOCUMENTS

| | | | | |
|---|---|---|---|---|
| CN | 109549627 A | 4/2019 | | |
| CN | 109758138 A | 5/2019 | | |
| CN | 110167430 A | 8/2019 | | |
| WO | WO-2022157542 A1 * | 7/2022 | | G16H 50/20 |

* cited by examiner

610
Start data reading

640
Continually measure
PPG pulse waveform

620
Read the
sweat data

630
Read the
temperature data

>5s

650
Convert PPG raw
data to heart rate

660
Data analysis

670
Output based on data analysis

680
Standby

Warm Up
No sweat    Start    Stable
            to
            sweat

Sweat Analyte Concentration

Unstable t1        t2
Time
(1) Begin to sweat

Sweating, stable data

Sweat Concentration

Time
(2) Sweating

900

1000

DEVICE FOR MONITORING HEAT STRESS

BACKGROUND

Heat stress refers a number of medical conditions which may be caused by the body overheating. Symptoms range from profuse sweating to dizziness, loss of consciousness and even death. People who are exposed to extreme heat or who work in hot environments may be at risk of heat stress, which can result in various occupational illnesses and injuries.

The main method of measuring heat stress is the wet-bulb globe temperate (WBGT) index, which uses measurements of environmental temperature to evaluate the risk of heat stress. The WBGT index models an apparent temperature and in one formulation is equal to $0.7\ T_w + 0.2\ T_g + 0.1\ T_d$, where $T_w$ is the natural wet-bulb temperature, $T_g$ is the globe thermometer temperature and $T_d$ is the dry-bulb temperature.

Wet bulb temperature is the temperature read by a thermometer covered in water-soaked cloth (a wet-bulb thermometer) over which air is passed. Globe thermometer temperature is the uniform temperature of an imaginary enclosure in which the radiant heat transfer from the human body is equal to the radiant heat transfer in the actual non-uniform enclosure and may be measured by a black globe thermometer. Dry-bulb temperature is the actual air temperature. Wet-bulb temperature is related to humidity and is the lowest temperature that can be reached under ambient conditions by the evaporation of water only.

By combining these different types of temperature, the WBGT index models cooling that may be achieved by evaporation of sweat and radiating of heat and gives a better measure of the effect of heat upon the body. Various organisations have published guidelines as to safety considerations at different levels of WBGT including recommended water intake and safe levels of physical activity.

SUMMARY

A first aspect of the present disclosure provides a wearable heat stress monitor comprising: a first sensor, the first sensor comprising an electrode for sensing a sweat parameter; at least one further sensor for sensing a body parameter or an environmental parameter; a processor to determine a heat stress level based on the sweat parameter sensed by the first sensor and the body parameter or environmental parameter sensed by the at least one further sensor; and an output module for outputting information based on the heat stress level determined by the processor.

The output module may for instance be a display or a wireless communications module. The front-end module may include circuitry to convert analogue signals from the sweat sensing electrode into digital signals and/or to condition analogue signals received from the sweat sensing electrode.

In some examples the front-end module may include a waveform generator to inject an excitation signal having a frequency to the sweat sensing electrode. In some examples, the front-end module or the processor may be configured to measure an admittance of the sweat based on a response of the sweat sensing electrode to the excitation signal. In some examples the front-end module or the processor may be configured to determine an analyte concentration of the sweat based on an electrical parameter measured by the sweat sensing electrode. A sweat analyte is a chemical constituent of the sweat. For instance the sweat analyte may be an electrolyte contained in the sweat.

A second aspect of the present disclosure provides a wearable heat stress monitor comprising: a first sensor comprising at least one sweat sensing electrode for contacting sweat of a user and an analogue front-end module electrically connected to the at least one sweat sensing electrode and configured for sensing an electrical parameter of the user's sweat. The heat stress monitor further comprises a processor to determine a heat stress level based on the electrical parameter of the sweat sensed by the front-end module and an output module for outputting information based on the heat stress level determined by the processor.

BRIEF DESCRIPTION OF THE DRAWINGS

Examples of the present disclosure will be explained below with reference to the accompanying drawings, in which:

FIG. 4B shows an example of a band including the heat stress monitor according to an example of the present disclosure;

FIG. 4C shows an example of a watch including the heat stress monitor according to an example of the present disclosure;

DETAILED DESCRIPTION

Various examples of the disclosure are discussed below. While specific implementations are discussed, it should be understood that this is done for illustrative purposes and variations with other components and configurations may be used without departing from the scope of the disclosure as defined by appended claims. In the context of the present disclosure the terms "a" and "an" refer to one or more of a particular element. The term "based on" means based at least in part on and the term "connected to" includes both direct connections between two components and indirect connections in which two components are connected via one or more intermediate components.

The WBGT index provides an objective measurement for assessing the risk of heat stress and has been the subject of many scientific studies. However, it is difficult to calculate and does not account for individual variances.

The present application proposes a portable heat stress monitor which may be worn by a user and give personalised feedback as to the risk of heat stress. In particular, according to various aspects of the disclosure, which are described below, the heat stress monitor comprises a sweat sensor and is configured to determine a heat stress level based on analysing a user's sweat. For instance, the sweat sensor may include an electrode and may be configured to sense a sweat parameter, such as an electrical characteristic of the user's sweat. This approach provides heat stress information which is tailored to the individual, as it is based on actual readings from the user's body, rather than relying solely on environmental information such as air temperature. Furthermore, the inventors have found that sweat content has a strong relationship to the risk of heat stress.

Figures 1, 2:
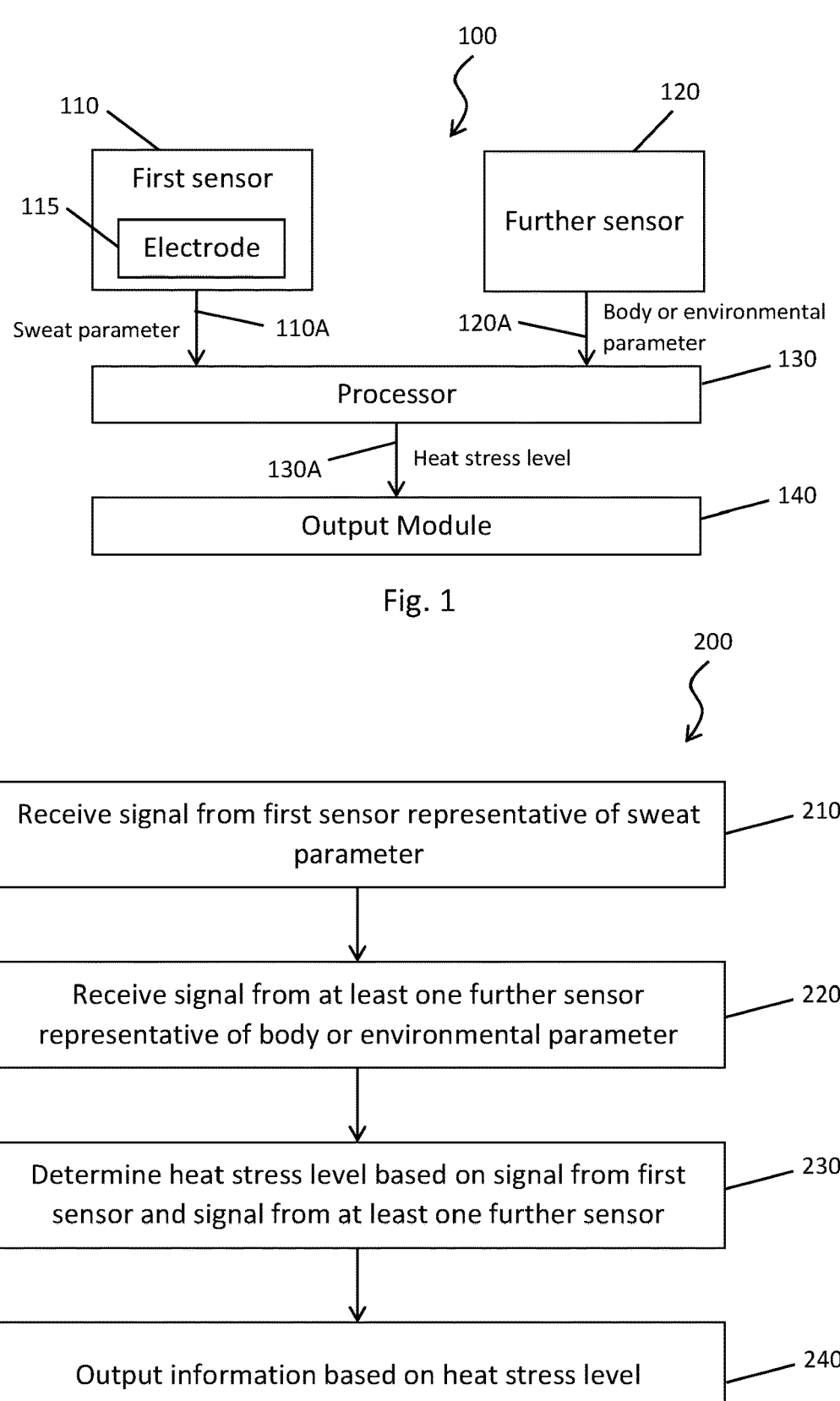
FIG. 1 is a schematic diagram showing components of a heat stress monitor according to an example of the present disclosure.
FIG. 2 shows an example method of determining a heat stress level by a heat stress monitor according to an example of the present disclosure.

FIG. 1 is a schematic diagram showing an example of a wearable heat stress monitor 100 according to the present disclosure. The heat stress monitor 100 comprises a first sensor 110 including an electrode 115 for sensing a sweat parameter and one or more further sensors 120 for sensing a body parameter or an environmental parameter. For instance the one or more further sensors 120 may comprise one or more of a body temperature sensor, a heart rate sensor and an environmental humidity sensor. The heat stress monitor 100 further comprises a processor 130 configured to determine a heat stress level based on the sweat parameter 110A sensed by the first sensor and the body parameter or environmental parameter 120A sensed by the one or more further sensors 120. The processor may for example comprise a central processing unit, microprocessor, field programmable gate array, application specific integrated chip or other logic circuitry. The heat stress monitor 100 also comprises an output module 140 for outputting information based on the heat stress level determined by the processor 130. For instance the output module may comprise a display and/or a wireless communications module, such as but not limited to a Wifi, Bluetooth, or wireless telecommunications module. In still other examples, the output module may comprise a wired communications module such as, but not limited to, a universal serial bus (USB) port or other wired connector.

FIG. 2 shows an example method 200 of determining heat stress level by a heat stress monitor according to an example of the present disclosure.

At block 210 the processor of the heat stress monitor receives a signal from the first sensor which is representative of a sweat parameter. For instance the signal may include an admittance or other electrical parameter of the sweat or a concentration of a sweat analyte as determined by the first sensor. A sweat analyte is a chemical constituent of the sweat. For instance the sweat analyte may be an electrolyte contained in the sweat.

At block 220 the processor receives a signal from at least one further sensor of the heat stress monitor, which is representative of a body parameter (e.g. body temperature or heat rate) or an environmental parameter (e.g. environmental humidity).

At block 230 the processor determines a heat stress level based on the signal from the first sensor and the signal from the at least one further sensor.

At block 240 the processor controls the output module to information based on the heat stress level determined in block 230. For instance, the output module may display the determined heat stress level, generate a visual or audio alert if a predetermined heat stress level is reched or exceeded or send data relating to the heat stress level to an external device.

As the heat stress monitor of FIG. 1 may form part of a wearable device, it may be carried by the user and may gather information directly from the user's body and their environment. Further, the device may be implemented with compact electronic components and thus does not require sophisticated medical or meteorological equipment, such as found in a hospital or laboratory. The device and above described method are able to measure several different parameters, including at least a sweat parameter and a body parameter or environmental parameter, and combine these different parameters to arrive at a heat stress level. As the device may take into account a variety of factors, including body sweat and other physiological or environmental parameters, it may measure heat stress (or the risk of heat stress) more accurately than methods which use temperature only or heart rate only.

The first sensor includes one or more sweat sensing electrodes. The electrodes may for example be bare metal electrodes or electrodes with a surface treatment for reacting with a particular sweat electrolyte. The electrodes may be positioned on or protrude through a surface of a main body of the wearable heat stress monitor, which surface faces the skin when the heat stress monitor is worn. In this way the one or more electrodes may contact epidermal sweat or have epidermal sweat in their proximity and electrical readings from the electrodes may be affected by the presence and qualities of the epidermal sweat.

The first sensor, also referred herein as the sweat sensor, may be used to measure an electrical characteristic of the sweat such as impedance, electrical resistance, conductivity, admittance etc. The electrical characteristic may itself be used as a sweat parameter, or a sweat parameter may be calculated based on the measured electrical characteristic. For instance a concentration of a particular sweat analyte in the sweat may be calculated based on a relationship between the electrical characteristic and the sweat analyte concentration. In one example the sweat sensor is configured to determine a concentration of a sweat analyte, such as but not limited to sodium chloride, sodium ions or chlorine ions.

In addition to the at least one sweat sensing electrode, the sweat sensor may comprise a front end module mention which is configured to determine a sweat parameter based on a signal received from the at least one sweat sensing electrode. For instance, the front end module may include a signal generator for injecting an electrical signal into at least one sweat sensing electrode and/or a measuring a response of the at least one sweat sensing electrode to the injected signal. In some examples, the front end module may include signal conditioning circuitry, such as one or more amplifiers or filters for amplifying a signal received from the at least one sweat sensing electrode and/or filtering out noise. The front end module may also include a digital to analogue converter for converting an analogue signal into a digital signal which can be input to the processor.

As mentioned above, the heat stress monitor is a wearable device. In some examples, the heat stress monitor may comprise a clip for fixing the heat stress monitor to an item of clothing in a position in which the electrode is proximate the skin of the user. In other examples, the heat stress monitor may be provided in a wearable band, e.g. the first sensor, at least one further sensor, processor and output module may all be provided on a band suitable for wearing on a user's limb or forehead. In other examples, the heat stress monitor may be integrated into a smart-watch. In still other examples, the heat stress monitor may be formed of micro-components integrated into an adhesive patch; for instance the first sensor, at least one further sensor, processor and output module may be provided on a flexible adhesive patch for attachment to the user's skin.

Figures 3, 4A:
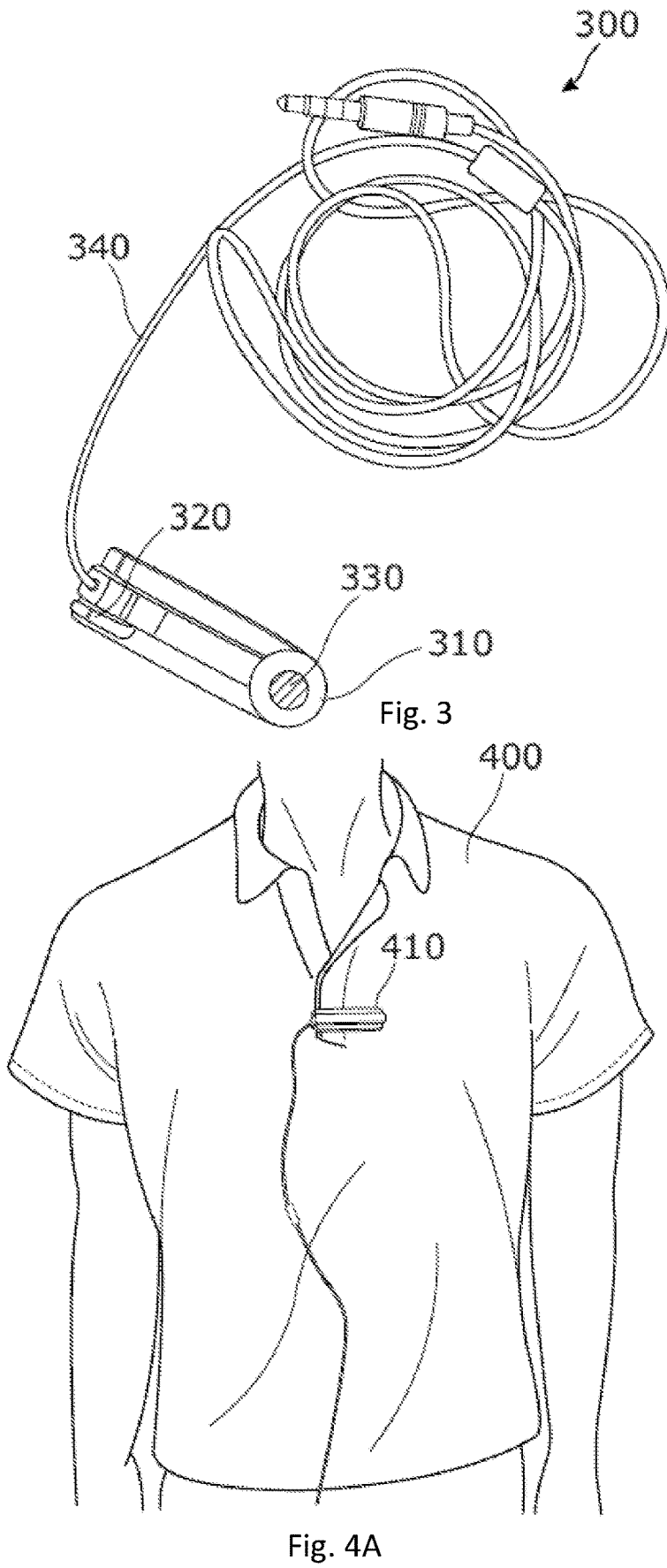
FIG. 3 shows an example of a device incorporating a heat stress monitor according to a further example of the present disclosure.
FIG. 4A shows an example of the device of FIG. 3 when worn by a person according to an example of the present disclosure.

FIG. 3 shows one example of a device 300 incorporating a heat stress monitor according to the present disclosure, in which the device is to be attached to the user's clothing. In the example of FIG. 3, the device includes a main body 310 and an electrode 330 on a surface of the main body. The electrode may comprise a pattern of electrical contacts on the surface of the main body and in some examples the electrode surface area may be surrounded by a spacer, such as a ring. The effective surface area of the electrode pattern may be relatively small, e.g. between 80 mm² to 150 mm². In the example of FIG. 3, the device 300 further includes a clip 320 for fastening to an item of clothing and an output cable 340 for output of data relating to heat stress. Thus the device may be fastened to an item of the user's clothing by the clip 320 with the electrode 330 facing the user's skin.

FIG. 4A shows an example of the device 300 when worn by a user 400 and fastened in a location near the user's chest. In other examples the device 300 could be worn in different locations on the body of the user. In still other examples, the device 300 may have a display and/or a wireless communication module for output of data relating to heat stress, instead of the wired output cable 340.

FIG. 4B shows another example, in which the heat stress monitor 410 is incorporated in a band 420 which wraps around the wrist or arm of a user. In this case the electrode 430 may be on a side of the band which faces the user's skin. FIG. 4C shows a further example in which the heat stress monitor is incorporated in a watch 440, in which case the electrode 450 may be located on a side of the watch strap or a side of the main watch body which faces the user's skin when the watch is worn. The devices of FIGS. 3 and 4A to 4C may comprise any of the features discussed described above in relation to FIGS. 1 and 2.

Figure 5:
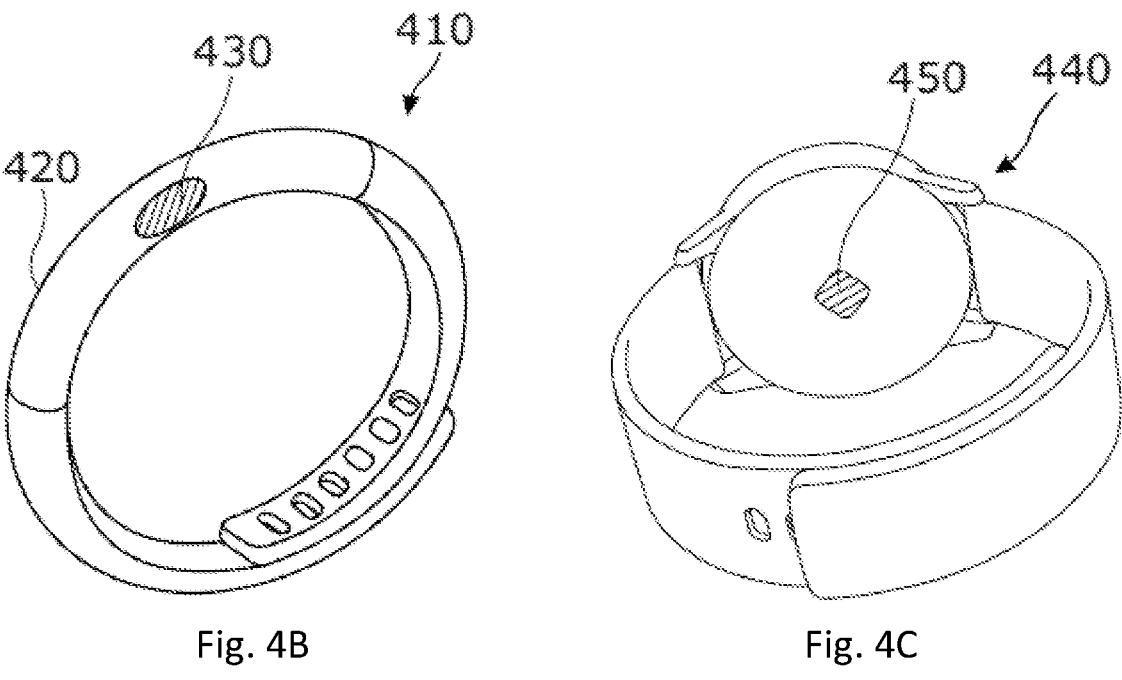
FIG. 5 is a schematic diagram showing components of a heat stress monitor according to an example of the present disclosure.
Figure 5:
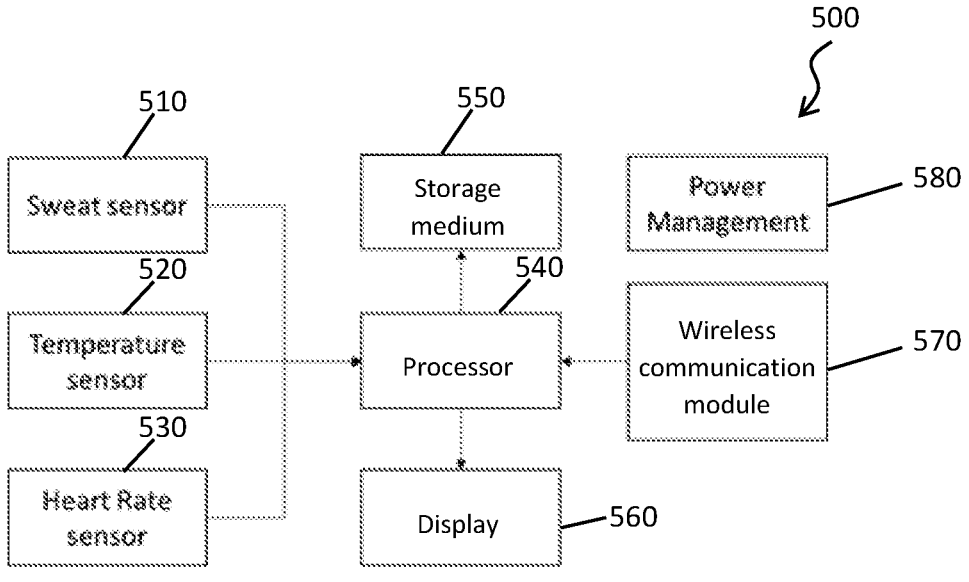

FIG. 5 shows a further example of a heat stress monitor 500 according to the present disclosure. The heat stress monitor comprises a sweat sensor 510, temperature sensor 520 and heart rate sensor 530 which are connected to a processor 540. The sensors and processor may include any of the features of the sensors and processor described in the examples above. The processor 540 is connected to a data storage 550 such as a random access memory (RAM), flash memory etc for storing heat stress data generated by the processor and/or measurements made by the sensors. The processor 540 is connected to a display 560 which acts as an output module and may display a heat stress level determined by the processor 540, an alert if a predetermined heat stress level is met or exceeded and/or other data. The processor is connected to a wireless communications module, such as a wifi or Bluetooth module, which may export heat stress data wirelessly to an external device. The heat stress monitor further includes a power management module 580 for supplying power to the various components.

Various examples of sweat sensor have already been discussed above. The heart rate sensor may be an electrical sensor such as an electrocardiogramsor or an optical sensor such as a photoplethysmography (PPG) sensor. A PPG sensor measures flow of blood by directing a light from a light source, such as a light emitting diode (LED), through the skin to a blood vessel and detecting how the light scatters. In some examples the PPG sensor may collect respiratory rate data as well as heart rate data and both the heart rate data and the respiratory data may be used to determine the heat stress level. The temperature sensor may be a MEMS based sensor, thermocouple sensor, resistance thermometer or other type of temperature measuring device. In some examples the skin temperature may be taken as the body temperature, while in other examples the skin temperature may be adjusted by a calibration factor to determine the body temperature. Such calibration factor may be based on calibration of the temperature sensor and/or a human body model.

Figures 6, 7A, 7B:
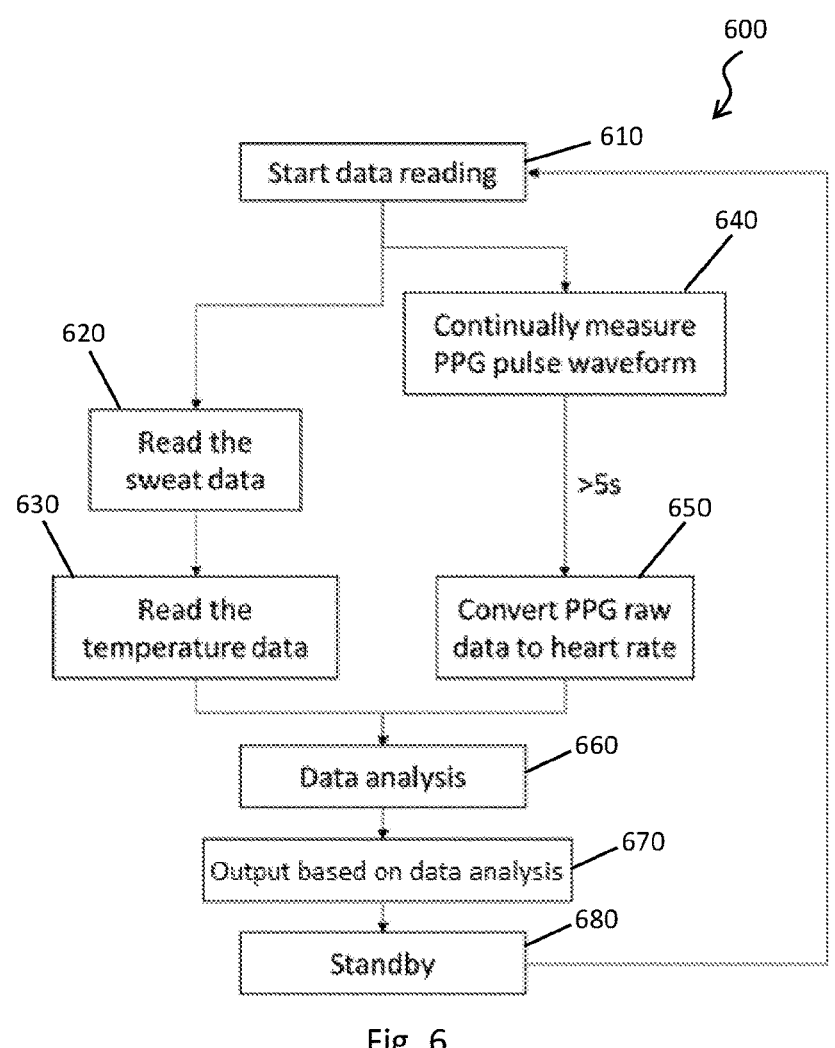
FIG. 6. shows a further example method of determining a heat stress level by a heat stress monitor according to an example of the present disclosure.
FIGS. 7A, 7B and 7C are graphs showing variation in sweat analyte concentration at a beginning stage of sweating, mid-stage of sweating and end-stage of sweating, as measured by heat stress monitor according to an example of the present disclosure.

FIG. 6 shows a further example of a method 600 of determining a heat stress level by a fitness monitor according to the present disclosure.

At block 610 the processor starts to read data from the sensors. For example, this may be in response to the user switching on the device or in response to a sensor activating the heat stress monitor in response to detecting a particular event, such as the presence of sweat or temperature or heart rate exceeding a predetermined threshold.

At block 620 the processor reads sweat data from the sweat sensor. At block 630 the processor reads temperature data from the temperature sensor. At block 640 the device continuously monitors a photoplethysmogram (PPG) waveform. At block 650 the PPG waveform is periodically converted into a heart rate value; in one example a heart rate value is calculated every 5 seconds, but a different period could be used in other implementations. Blocks 640 and/or 650 may be performed by electronic or logical circuitry of the heart rate sensor itself, or by the processor if the processor receives raw data from the heart rate sensor.

At block 660, the processor performs data analysis on the sweat data, temperature data and heart rate data. Based on this data analysis, the processor may determine a heat stress level of the user, predict a future heat stress level of the user and/or generate an alert if the current heat stress level or a future predicted heat stress level exceeds a predetermined value.

At block 670, the heat stress monitor generates an output based on the data analysis of block 660. For example, the processor may control the display to display a heat stress level or an alert and/or control a wired or wireless output module to output a result of the data analysis to an external device.

At block 680, the heat stress monitor goes into standby, for instance if it is switched off by the user.

As explained above, the heat stress monitor determines a heat stress level of the user based on a number of different factors, including at least a sweat parameter and one or more body parameters and/or environmental parameters. This may be achieved in many ways. For instance the parameters may be compared to predetermined thresholds, entered into a predetermined formula, compared with a look-up table or entered into an artificial intelligence engine to determine the heat stress level or a combination of these methods. The following discussion is provided by way of example only.

In one example, the processor is configured to determine the heat stress level based on the sweat parameter sensed by the first sensor multiplied by a piecewise function.

A piecewise function is a function which classifies input values as belonging to one of a plurality of domains and determines an output value in a first way for a first domain of input values and a second way for a second domain of input values. By using a piecewise function the contribution to the heat stress calculation from the sweat parameter may be modified depending on the flow rate, stage of sweating or other characteristics of the sweat.

In some examples, the sweat sensor may measure a sweat parameter, such as an electrical characteristic of the sweat, or a sweat analyte concentration, but be unable to directly detect the volume of sweat or rate of sweating. The inventors have discovered that even when the volume or rate of sweating cannot be directly detected, the stage of sweating may be inferred based on electrical characteristics of the sweat and/or sweat analyte concentration. Therefore by assigning appropriate values to the piecewise function, the processor can vary the weight given to the sweat parameter depending on the stage of sweating. For instance the piecewise function may have a zero value when the sweat concentration meets a first criteria and a second value when the sweat concentration meets a second criteria.

In one example the heat stress level may be expressed as:

$$Heat\ Stress = ks \qquad Equation\ 1$$

where k is the piecewise function and s is the sweat analyte concentration.

The piecewise function may be dependent on a behaviour of the sweat and may for instance be used to filter out initial or final stages of sweating which might otherwise give inaccurate results.

In some examples the piecewise function may have a zero value when the sweat concentration is fluctuating and a non-zero value when the sweat concentration is stable, increasing in a non-fluctuating manner or decreasing in a non-fluctuating manner. This may for instance be expressed as shown in Equation 2.

$$k(s) = \begin{cases} 0, \text{if } s \text{ is unstable, } e.g. \text{ rapidly fluctuating} \\ s, \text{if } s \text{ is not fluctuating} \end{cases} \qquad Equation\ 2$$

Figure 7C:
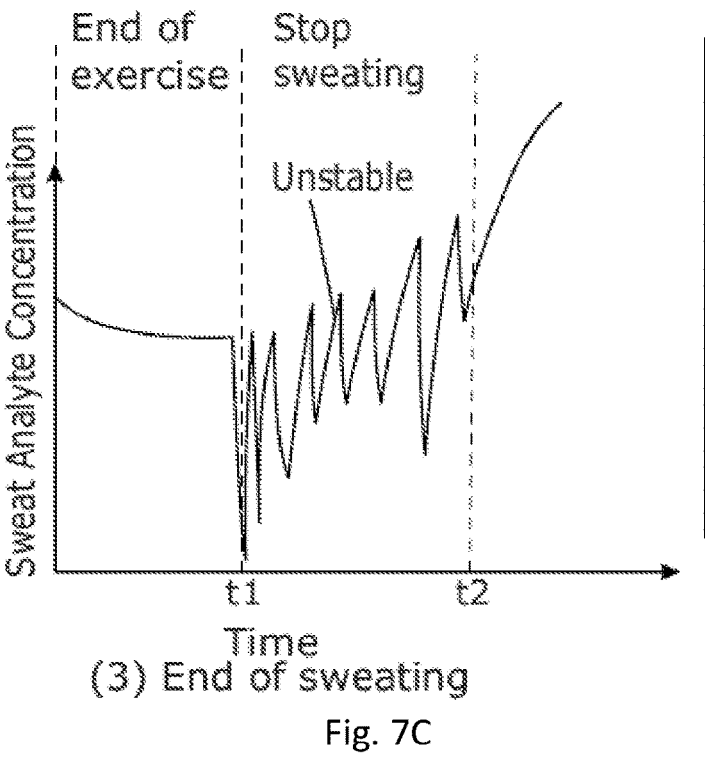

FIGS. 7A to 7C are a series of graphs showing sweat analyte concentration (y-axis) against time (x-axis) at different stages of the sweating process.

FIG. 7A shows an example of sweat analyte concertation over time at a beginning stage of sweating, such as when a person starts to exercise. It can be seen that the analyte concentration is initially zero, but rises steeply and starts to fluctuate rapidly between times t1 and t2. After time t2 the analyte concentration is relatively stable. Prior to time t1 the data is not reliable, as either there is no sweat or only a small quantity of sweat such that the analyte concentration may increase rapidly due to evaporation rather than changes in the physiological state of the person being monitored.

FIG. 7B shows an example of sweat analyte concertation over time during normal sweating, e.g. after a person has been exercising or exposed to heat for a while. It can be seen that the analyte concentration changes slowly over time and in this example the analyte concentration gradually increases.

FIG. 7C shows an example of sweat analyte concertation over time at an end stage of sweating, e.g. after a person stopped exercising and started to cool down. It can be seen that between times t1 and t2 the analyte concentration fluctuates rapidly. After time t2 the data is not reliable as the person has stopped sweating and changes in concentration are mainly due to evaporation.

While FIGS. 7A-7C show an example of variation of sweat analyte concentration, similar patterns occur with other sweat parameters, such as admittance, impedance, voltage, current or other electrical characteristics with unstable variation or rapid fluctuation at the beginning and end of sweating and more stable periods in between, Thus by detecting rapid fluctuations in the sweat parameter (e.g. sweat analyte concentration) the device is able to distinguish between different stages of sweating. Sweat parameter data collected when the sweat parameter is unstable or rapidly fluctuating may be filtered out or disregarded. However, sweat parameter data which is stable or which changes more slowly over time may be kept, as such changes may be due to changes in intensity of exercise or increased heat stress. In summary, fluctuations above a predetermined amplitude and/or above a predetermined frequency may be considered to be rapid fluctuations which indicate a beginning of sweating stage or an end of sweating stage and such data may be disregarded. The threshold for predetermined amplitude or predetermined frequency will depend on the particular sweat parameter and the circuitry used to monitor the sweat parameter. Such thresholds may be set based on testing the device on a range of subjects and exercise conditions. In one example, the frequency threshold may be set to 100 Hz, while in other examples a lower frequency threshold such as 90 Hz or 50 Hz may be used.

In order to improve the accuracy of the determination of heat stress level, the processor may be configured to detect periods of instability when the sweat parameter is unstable (e.g. the rapidly fluctuating periods) and disregard sweat parameter values sensed in said periods of instability when determining the heat stress level. Further, the processor may be configured to detect an initial stage of sweating (e.g. up to t2 in FIG. 7A) and an end stage of sweating (e.g. after t1 in FIG. 7C) based on fluctuations in the sweat parameter and disregard sweat parameter values sensed in the initial and end stages of sweating when determining the heat stress level.

For example, sweat parameter data from periods of rapid fluctuation (e.g. t1 to t2 in FIGS. 7A and 7C) may be disregarded by setting the piecewise function to 0 for such periods. Furthermore, sweat parameter data collected before the initial rapid fluctuation period (e.g. before t1 in FIG. 7A) and after the end of sweating rapid fluctuation period (e.g. after t2 in FIG. 7C) may be disregarded, e.g. by setting the piecewise function k to 0 for such periods. In some examples the rapidly fluctuating periods may be detected based on thresholds as described above, while in other examples an artificial intelligence engine may be trained to detect rapidly fluctuating periods and set the piecewise function accordingly. In some examples the piecewise function may be set to zero in other conditions when the sweating is considered not to be in a stable state. For example, the piecewise function may be set to zero if the sweat parameter is below a lower threshold which may be a threshold below which the data is not considered meaningful, e.g. if the sweat parameter is close to zero or below an expected normal lower range expected for sweat. Further, the piecewise function may be set to zero if the sweat parameter is above an upper threshold which the sweat parameter would usually not be expected to reach.

As the device tracks the change of the sweat parameter (e.g. analyte concentration) and fluctuations over time, the device is able to detect when a user starts and stops sweating. Further by using other inputs such as body temperature or heart rate, the device is able differentiate between the situation where the user has no sweat due to not having exercised and the situation where the user has no sweat due to having finished exercising. By combining determination of sweating stage based on the sweat parameter (e.g. sweat analyte concentration) with other parameters the processor is able to differentiate various scenarios which may be difficult to differentiate from the sweat parameter alone. For instance in response to detecting that the user has stopped sweating and detecting a drop in the user's heart rate and/or body temperature, the processor may determine that the user is cooling down after exercise. However, in response to detecting that the user has stopped sweating, but the user's heart rate and/or body temperature remains high (i.e. above a certain threshold) or rise after the stop of sweating, the processor may determine that the user is experiencing heat stroke.

In some examples the processor may be configured to determine the heat stress level by summing the sweat parameter (e.g sweat analyte concertation) or product of sweat parameter and piecewise function over time. This models how the risk of heat stress is greater, when the user has been sweating for a longer period of time.

In some examples, the processor may be configured to determine the heat stress level based on normalised values of each parameter, e.g. a normalised value of the sweat parameter, normalised value of the body temperature parameter and normalised value of the heart rate parameter. That is each of these parameters may be normalised to the same scale, e.g. between 0 and 100.

For example, normal body temperature is between 36.5-37.5° C., while normal resting heart rate for an adult is between 60 and 100 beats per minute (bpm) and maximum heart rate for an adult (the heart rate achievable through exercise without serve problems) depends on age but is generally between 160 and 200 bpm. Thus a difference of a 2 bpm in heart rate will not greatly impact the risk of heat stress, but a difference in body temperature of 2° C. will have a great impact. Thus by normalising the measured values of each parameter to a normal range for the parameter, the processor is able to determine which changes in parameter values are significant.

In some examples, the processor is configured to determine the heat stress level based on applying a respective weighting to each parameter. In this way, even after normalisation, some parameters may be given greater weight than others when determining the heat stress level. As the sweat parameter has been found to be a particularly accurate way of predicting heat stress, in some implementations the sweat parameter may be given a greater weight than the weighting(s) applied to the other parameter(s).

In one example, the processor is configured to use the following formula to determine the heat stress:

$$\text{Heat Stress} = w_1 a_1 \sum_{t=0}^{now} kst + w_2 a_2 HR + w_3 a_3 T_{body} \qquad \text{Equation 3}$$

where:
  s is the sweat parameter, e.g. sweat analyte concentration;
  $T_{body}$ is the body temperature parameter;
  HR is the heart rate parameter;
  k is the piecewise function for sweat;
  t is the time elapsed since beginning of the monitoring;
  $a_1$, $a_2$ and $a_3$ are normalized correlation functions for implementing the normalisations for each parameter; and
  $w_1$, $w_2$ and $w_3$ are weighting functions for applying the weightings to each parameter.

As noted above, the weighting applied to the sweat may be greater than the weightings applied to the other parameters. For instance, in some examples the weight applied to the sweat parameter may be 60% or more of the total weightings. In some examples, when the piecewise function k is zero, so that there is no contribution to the calculation from the sweat parameter, the weightings (e.g. $w_2$ and $w_3$) applied to the other parameters may be increased, e.g. to make up 100%. For example, before the user has started sweating steadily the sweat piecewise function may be zero such that there is no contribution to the heat stress calculation from the sweat parameter; in such cases the weightings for the heart rate and body temperature parameters may be increased so heat stress can be detected, albeit less accurately, even in the absence of sweat parameter data. For instance, an alert may be generated if the heart rate and/or temperature reach a dangerous level.

It is to be understood that Equation 3 above is just an example and variations are possible while still keeping within the scope of the present disclosure. For instance, further body parameters and/or environmental parameters may be taken into account. In other examples the heat stress may be calculated based on the sweat parameter alone, or based on the sweat parameter in combination with the body temperature (but not heart rate), or based on the sweat parameter in combination with the heart rate (but not body temperature), or based on the sweat parameter in combination with one or more environmental parameters (such as humidity) etc., depending on the design of the device and the number and type of sensors which the device includes.

Figure 8:
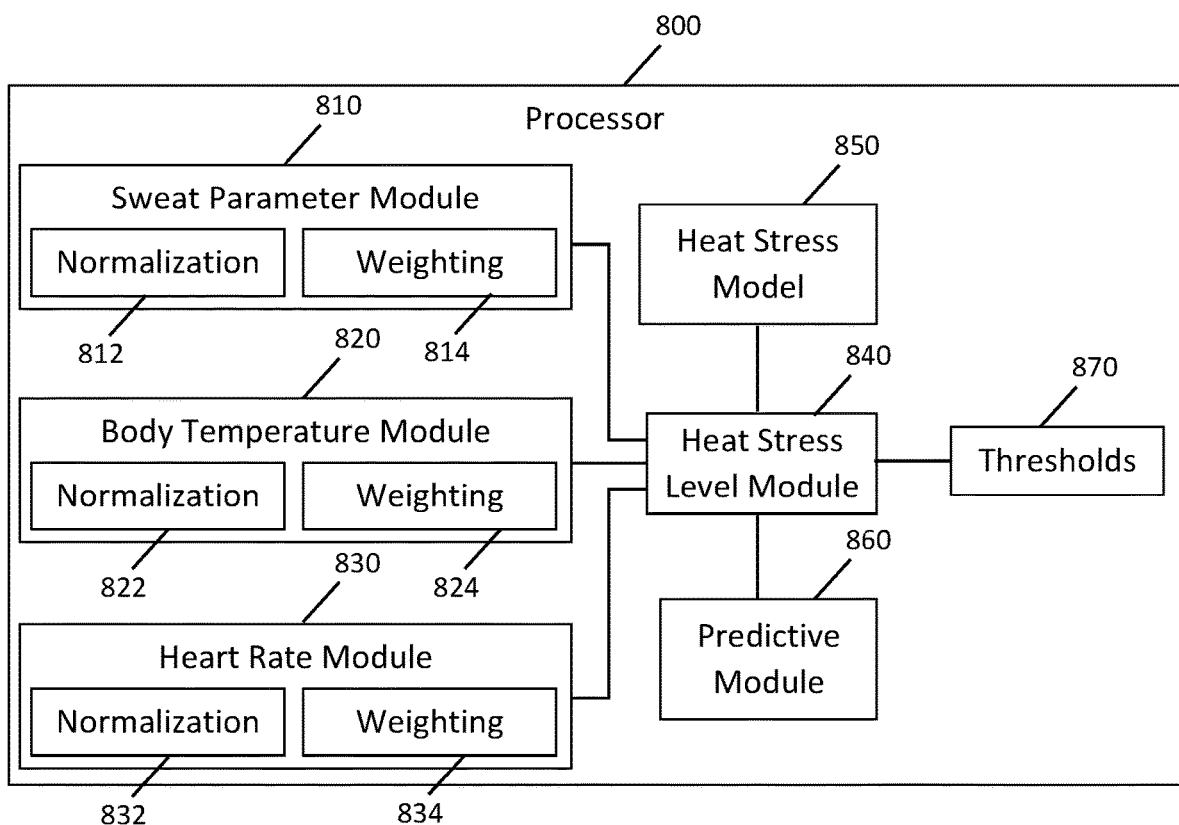
FIG. 8 is a schematic diagram showing an example of processor of a heat stress monitor according to an example of the present disclosure.

FIG. 8 is a schematic diagram showing an example of a processor 800 of a heat stress monitor according to an example of the present disclosure. The processor is configured to determine a heat stress level of the user based on sweat parameters measured by a sweat sensor, body temperature sensor and a heart rate sensor. The processor may comprise a microprocessor, central processing unit, ASIC, FPGA or other type of logic chip. The processor may further comprises a data storage medium such as memory for storing instructions executable by the processor. As shown in FIG. 8, the processor comprise a plurality of modules which may be implemented by logic hardware of the processor and/or by logic hardware of the processor in combination with machine readable instructions stored in the data storage medium.

The processor 800 includes a sweat parameter module 810 for receiving data representative of a sweat parameter measured by the sweat sensor. The sweat parameter module comprises a normalisation module 812 for normalising the sweat parameter and a weighting module 814 for applying a weighting to the normalised sweat parameter. The normalised, weighted sweat parameter is then output from the sweat parameter module to the heat stress level module 840.

The processor 800 may further include a body temperature parameter module 820 for receiving data representative of a body temperature parameter measured by the body temperature sensor. The body temperature parameter module comprises a normalisation module 822 for normalising the sweat parameter and a weighting module 824 for applying a weighting to the normalised body temperature parameter. The normalised, weighted body temperature parameter is then output from the body temperature module to the heat stress level module 840.

The processor 800 may further include a heart rate parameter module 820 for receiving data representative of a heart rate parameter measured by the heart rate sensor. The heart rate parameter module comprises a normalisation module 822 for normalising the heart rate parameter and a weighting module 824 for applying a weighting to the normalised heart rate parameter. The normalised, weighted heart rate parameter is then output from the heart rate module to the heat stress level module 840.

The normalisation modules and weighting modules may be apply the normalizations and weightings which have been described in the examples above.

The heat stress level module 840 is configured to determine a heat stress level of the user based on the normalised, weighted sweat parameter, body temperature parameter and heart rate parameter. This heat stress level module may apply any of the approaches described above to calculate the heat stress level. For instance, the heat stress level module may compare the parameters to predetermined thresholds, enter the parameters into a predetermined formula (such as, but not limited to Equation 3), compare the parameters with a look-up table or enter the parameters into an artificial intelligence engine to determine the heat stress level or a combination of these methods.

The processor may further comprise a heat stress model 850, which may for example store a look up table, parameter thresholds for different levels of heat stress, data such as neural network weights for an artificial intelligence engine or formulas and criteria for determining levels of heat stress etc. The processor 800 may further comprise a predictive model 860 for predicting a future level of heat stress based on the current and historical levels of heat stress and measured parameters. The processor 800 may further comprise a data storage for storing heat stress level thresholds 870 at which alerts should be generated (e.g. dangerous levels of heat stress). The heat stress level module may be configured to generate an alert to be output via the output module of the heat stress monitor in response to a current heat stress level or predicted future heat stress level of the user reaching or exceeding one of these thresholds.

As noted above, the processor 800 may be configured to generate a projected future value of the heat stress level based on heat stress levels determined for previous time periods. This projection of future level of heat stress may be carried out by a predictive module of the processor, such as the module 860 shown in FIG. 8.

In some examples, the processor may be configured to generate the projected future value of the heat stress level based on a gradient of the heat stress level over previous time periods.

This approach is illustrated with reference to several examples in FIG. 9. The graph shows the change in heat stress level over time for three individuals as determined by a device according to an example of the present disclosure. The heat stress level is rated between 0 and 4 on the y-axis, while the x-axis represents time in minutes. The heat stress level values for the first individual are shown by the trend line 910 in which data points are marked with triangles. The heat stress level values for the second individual are shown by the trend line 920 with data points marked with squares and the values for the third individual by the trend line 930 with data points marked by circles. The solid parts of each trend line represent actually measured values, while the dotted parts of each trend line indicate projected future values based on the past trend.

Figure 9:
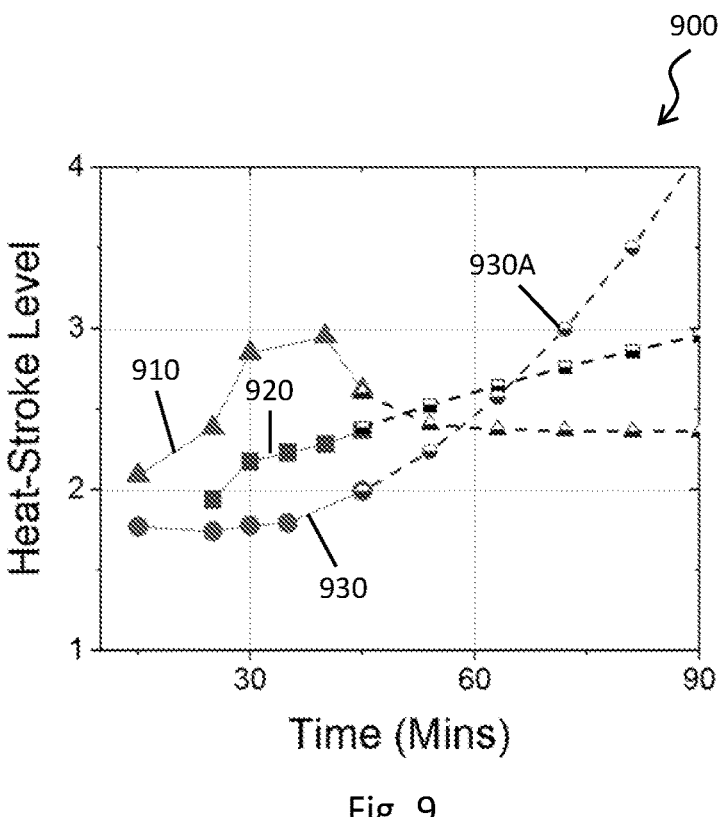
FIG. 9 is a graph showing variation of heat stress level over time for three individuals as measured by a heat stress monitor according to an example of the present disclosure.

In the example of FIG. 9, the projected future values of heat stress level are predicted by extrapolating the trend based on a gradient of the heat stress level over previous time periods. Thus it is presumed the heat stress level will increase or decrease according to a straight line gradient determined based on a number of previous time periods. However, other modelling techniques could be used to predict the future heat stress values based on mathematical modelling of the trend, physiological models of heat stress and/or by applying machine learning to data sets collected from individuals wearing the device under controlled conditions. The predictive model may thus use artificial intelligence, curve extrapolation techniques or physiological models to predict future heat stress levels for an individual based on heat stress levels determined by the device in previous time periods of a same exercise or heat exposure session.

The processor may be configured to cause the output module to generate an alert indicating a risk of dangerous heat stress in response to the projected future value of the heat stress level exceeding a predetermined threshold.

Heat stress occurs in a number of distinct stages including heat camp, heat exhaustion and severe heat stress (such as heat stroke), each of which has different characteristics. While such conditions have medical definitions and may be assessed in a hospital environment, it is possible to model them in terms of a limited number of parameters such as body temperature, heart rate and sweat parameter etc. The processor may be configured to determine whether a user is in a heat cramp stage, heat exhaustion stage or a severe stage of heat stress based on a model of heat stress response, the sweat parameter determined by the first sensor (i.e. sweat sensor) and the parameter(s) sensed by the at least one other sensor.

In one example, the processor is configured to determine the user is at the heat cramp stage in response to the sweat parameter (e.g. sweat analyte concentration) being above a first threshold and a heart rate parameter being equal to or above a second threshold. The second threshold may be set based on medical data relating to heat cramp collected by the manufacturer. In one example the second threshold may be 50% of the maximum heart rate of the user (maximum heart rate may be determined based on age or other data).

In one example, the processor is configured to determine that the user is at the heat exhaustion stage in response to determining that the sweat parameter is above a third threshold (e.g. a concentration of sweat analyte associated with the skin being clammy), while the temperature parameter is equal to or above a fourth threshold, but below a fifth threshold. The fourth and fifth thresholds may be set based on medical data relating to heat exhaustion collected by the manufacturer. In one example the fourth threshold may be normal body temperature or a threshold slightly lower than normal body temperature, e.g. 37 degrees Celsius. In one example the fifth threshold is approximately 39° C. The determination that the user is at the heat exhaustion stage may be dependent upon the processor having previously determined the user was in the heat cramp stage.

The processor may be configured to determine that the user is at the heat stroke stage (i.e. extreme heat stress) when subsequent to detecting heat cramp or heat exhaustion, the sweat parameter sensed by the first sensor enters an abnormal range and the body temperature exceeds a sixth threshold. The sixth threshold may be set based on medical data relating to heat stroke collected by the manufacturer. In one example the sixth threshold is approximately 103° F. or 39.44° C. Thus the processor is able to detect heat stroke based on a high body temperature and unusual sweating behaviour such as a sudden cessation of sweat.

For example, where the sweat parameter is a sweat analyte concentration, the abnormal range may be defined as below a lower limit of 0.01 times the normal value or more than upper limit of 100 times the normal value). The normal concentration of NaCl in human saline solution is 0.9%, so for NaCl the abnormal range of concentration in sweat for the purposes of determining heat stroke would be below 0.009% or above 90%. It should be noted that, even where the piecewise function has gone to zero due to rapid fluctuation or abnormal sweating as often occurs in heat stroke, the sweat parameter (e.g. NaCL concentration) may still be monitored by the sweat sensor and made available to the processor. Thus the processor is able to detect the abnormal sweat analyte concentration and factor it into the determination of heat stroke.

The various thresholds used in determining the heat stress stage, including the first to sixth thresholds, follow the general pattern described above but may refined and further determined based on tests and calibration of the device.

As noted above, in some examples the processor may be configured to use a machine learning model to determine the heat stress level, projected future heat stress and/or heat stress stage.

Figure 10:
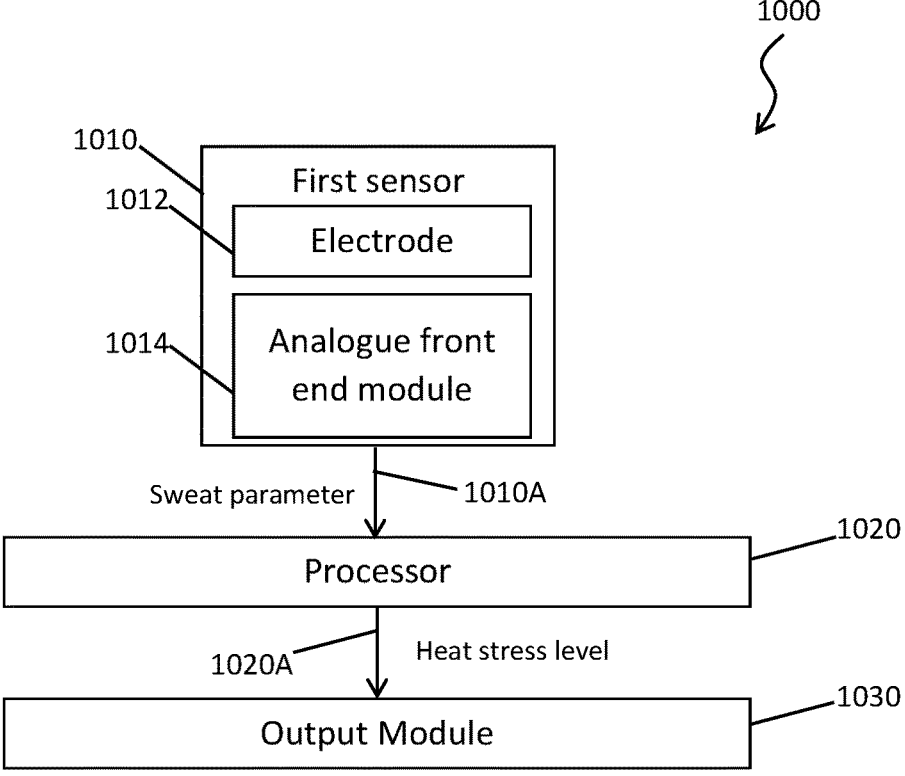
FIG. 10 is a schematic diagram showing components of a heat stress monitor according to a further example of the present disclosure.

FIG. 10 is a schematic diagram showing components of a heat stress monitor 1000 according to a further example of the present disclosure.

The wearable heat stress monitor 1000 comprises a first sensor 1010 comprising at least one sweat sensing electrode 1012 for contacting sweat of a user and an analogue front-end module 1014 electrically connected to the at least one sweat sensing electrode and configured for sensing an electrical parameter of the user's sweat. The heat stress monitor further comprises a processor 1020 for determining a heat stress level based on the electrical parameter of the sweat sensed by the front-end module and an output module 1030 for outputting information based on the heat stress level determined by the processor. Thus the heat stress monitor 1000 of FIG. 10 is similar to the heat stress monitor of FIG. 1 except that it does not have the one or more further sensors, but rather relies on output of the sweat sensor to the determine the heat stress level.

The heat stress monitor of FIG. 10 may have any of the features and operate in accordance with any of the methods described in the other examples above. In particular the sweat sensor, sweat sensing electrode and parts of the processor relating to processing measurements from the sweat sensor may be as described in the examples above.

Various modifications are possible. For instance, a second sensor for sensing a body temperature may be added to the heat stress sensor of FIG. 10 and the processor configured to determine the heat stress level based on the electrical parameter of the sweat sensed by the first sensor and the body temperature sensed by the second sensor. In addition to or instead of the body temperature sensor, a further sensor for sensing a heart rate may be added and the processor configured to determine the heat stress level based on the electrical parameter of the sweat sensed by the first sensor and the heart rate sensed by the further sensor.

The heats stress monitor of the present disclosure, in all of the examples described above with reference to FIGS. 1-10 comprises a sweat sensor which includes at least one electrode. Various illustrative examples of possible sweat sensor structures are described below by way of example only, but the present disclosure is not limited to any one of these examples and variations and modifications are possible with the scope of the present disclosure.

In some examples, the sweat sensor may include one or more sweat sensing electrodes and a front end-module. The front-end module may include circuitry to convert analogue signals from the sweat sensing electrode into digital signals and/or to condition analogue signals received from the sweat sensing electrode. For instance, the front-end module may comprise a plurality of electronic components, such as a filters, resistors, capacitors, amplifiers, an analogue to digital converter and/or a waveform generator. The processor may comprise a processor, such as a central processing unit, microprocessor or logic chip, together with one or more supporting components such as resistors, capacitors, a memory etc.

The sweat sensing electrode may comprise one or more bare metal electrodes and/or one or more electrodes with a surface treatment for reacting with a particular sweat electrolyte. The electrode(s) may be positioned on or protrude through a surface of the device so that the electrodes may contact epidermal sweat of the user and the front-end module may take electrical readings from the electrode(s) which electrical readings are affected by the presence and qualities of the epidermal sweat.

The sweat sensing electrode(s) together with the front-end module may thus be capable of detecting various electrical parameters of the sweat depending on the type of electrodes used. The sweat sensing electrode(s) together with the front end module may be used to measure an electrical parameter of the sweat, such as an impedance of the sweat, electrical resistance of the sweat, conductivity of the sweat, admittance of the sweat and/or a current passing through the sweat from a first electrode to a second electrode or a potential difference between a first electrode and second electrode.

FIGS. 11A to 11D below show example arrangements of the sweat sensing electrode(s) and front-end module, but it is to be understood these are examples only and other implementations and variations are possible within the scope of the present disclosure. For instance different arrangements of circuitry for measuring the electrical sweat parameters are possible. Furthermore, amplifiers, signal conditioning components, an analogue to digital converter and/or logical circuitry could be added to the front-end module.

Figure 11A:
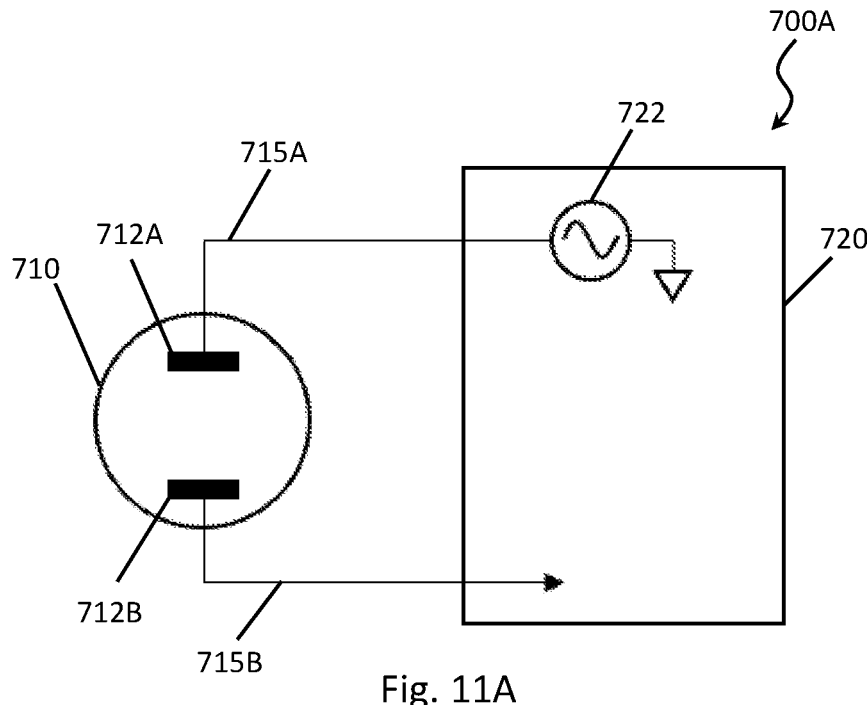
FIGS. 11A to 11D are schematic diagrams showing example structures of sweat sensors according to examples of the present disclosure.

FIG. 11A shows an example of sweat sensor 700A for measuring an electrical parameter of epidermal sweat. The sweat sensor includes a pair of sweat sensing electrodes 712A, 712B and an analogue front end module 720 comprising a signal generator 722. The signal generator 722 is configured to generate an input signal which may be a DC current or an AC current (i.e. an excitation frequency). The input signal may be injected into the first sweat sensing electrode 712A via a conductive line 715A connecting the first sweat sensing electrode 712A with the analogue front end module. The second sweat sensing electrode 712B is connected to the analogue front end by a second conductive line 715B which may detect a signal output from the second sweat sensing electrode. Thus the first electrode 712A acts as a working electrode and the second electrode 712B acts as a counter electrode.

The electrical parameter of the epidermal sweat, such as conductance or admittance etc., may be determined based on the signal output from the second sweat sensing electrode 712B. For instance, a known current may be injected into the epidermal sweat by the first 712A and the analogue front end 720 may measure a voltage drop between the signal injected into the first electrode 712A by the analogue front end module and the signal received from the second electrode 712B by the analogue front end module, and/or a current flowing between the first and second electrodes 712A, 712B. Use of an alternating current (AC) input signal with a high frequency may provide a more accurate measurement, as AC helps to reduce electrode polarization and Faradic and double layer capacitance at the electrodes is less at higher frequencies.

Figure 11B:
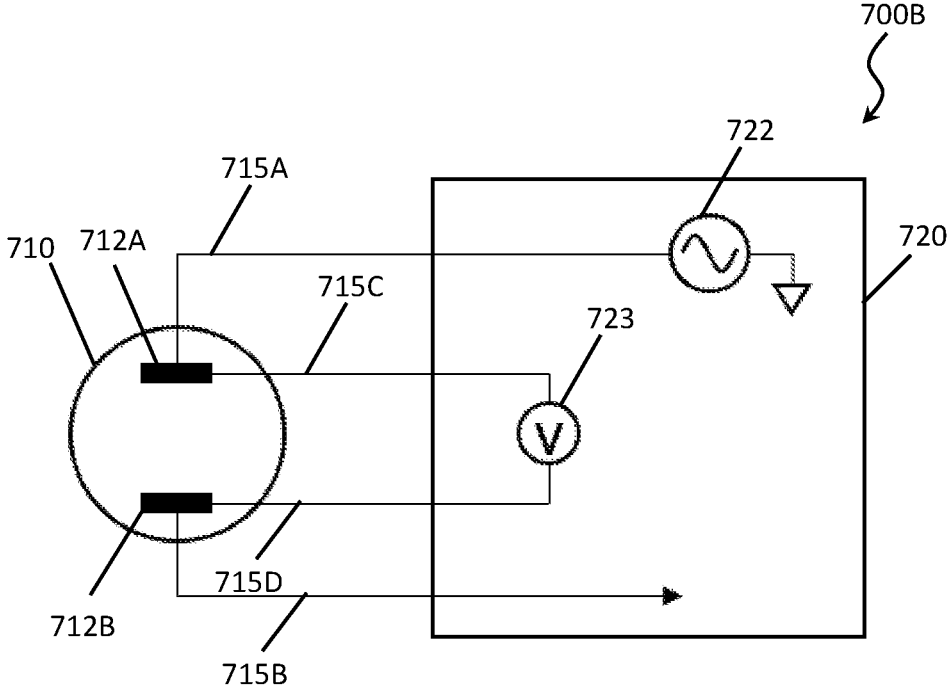

FIG. 11B shows another example of a sweat sensor 700B for measuring an admittance of epidermal sweat. The sweat sensor includes a pair of sweat sensing electrodes 712A, 712B, an analogue front end module 720 including a signal generator 722 and conductive lines 715A, 715B, similar to FIG. 7A, which parts are the same as in FIG. 7A. In addition, the example of FIG. 7B includes a voltmeter 723 for measuring a potential difference between the first sweat sensing electrode 712A and the second sweat sensing electrode 712B. The first sweat sensing electrode 712A may be connected to the voltmeter 123 by a third conductive line 715C and the second sweat sensing electrode 712B may be connected to the voltmeter 123 by a fourth conductive line 715D.

The arrangement of FIG. 11B is similar to that of FIG. 11A, but while FIG. 11A is a two point method, FIG. 11B is a four point method as a pair of electrodes 712A, 712B is used to inject the current into the sample and meanwhile the same pair of electrodes 712A, 712B is used to measure the resulting voltage drop. In principle, because no current flows through the voltmeter 723, the injected current completely flows through the sample and therefore, the contact resistance between each electrode 712A/712B and the respective conducting line 715C/715D is largely counteracted. Thus, in FIG. 7B, an electrical parameter of the epidermal sweat, such as conductance or admittance etc., may be determined based on the signal output from the second sweat sensing electrode 712B.

Figure 11C:
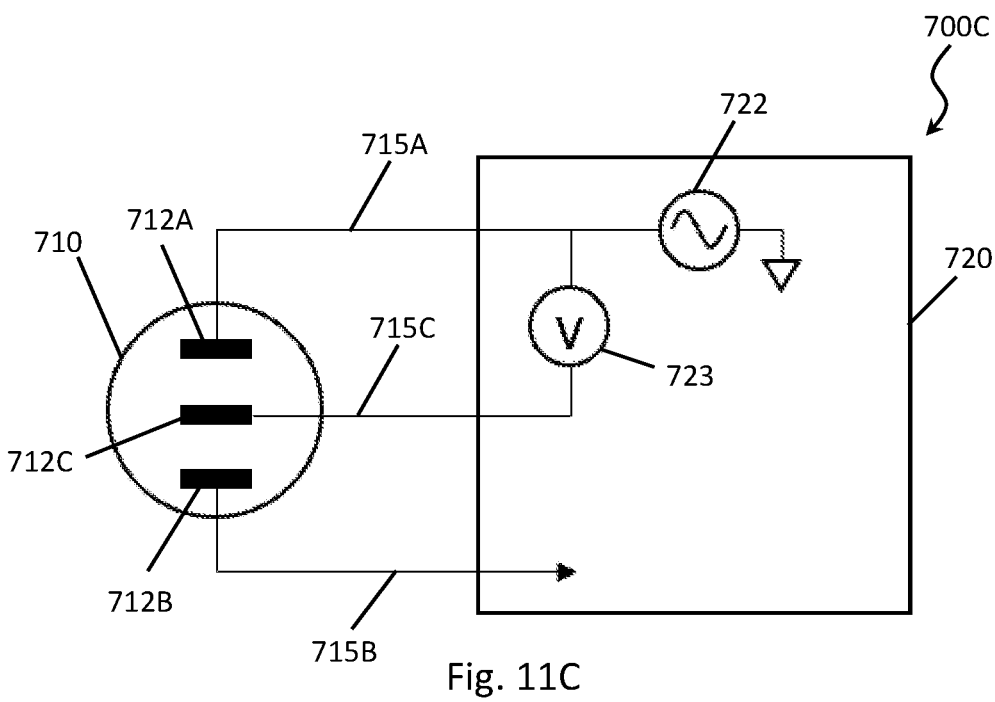

FIG. 11C shows an example of a sweat sensor 700C for measuring a current and potential difference between two electrodes. The sweat sensor includes three sweat sensing electrodes 712A, 712B and 712C and an analogue front end module 720 including a signal generator 722 and a voltmeter 723. The first sweat sensing electrode 712A and the second sweat sensing electrode 712B are connected to the signal generator 722 and a ground of the analogue front end 720 in the same way as for the arrangement of FIG. 11A described above. The voltmeter 723 is arranged to measure a potential difference between the first electrode 712A and the third electrode 712C, which is a reference electrode. The voltmeter may for example be connected to the first electrode 712A by the first conductive line 715A and the third electrode 712C by a third conductive line 715C. An electrical parameter of the epidermal sweat may be determined based on the current signal output from the second electrode 712B, the potential difference between the first electrode 712A and second electrode 712B and/or the potential of the third electrode 712C compared to the first or second electrode.

FIG. 11C, is a three point solution as the first, second and third electrodes, 712A, 712B, 712C act as working, counter and reference electrodes respectively. Three-electrode setups have the advantage that, due to the reference electrode they are able to measure potential changes of the working electrode independently of any changes that occur at the counter electrode. That is they are able to specifically measure a parameter of the part of the sweat sample between the working and reference electrodes.

Figure 11D:
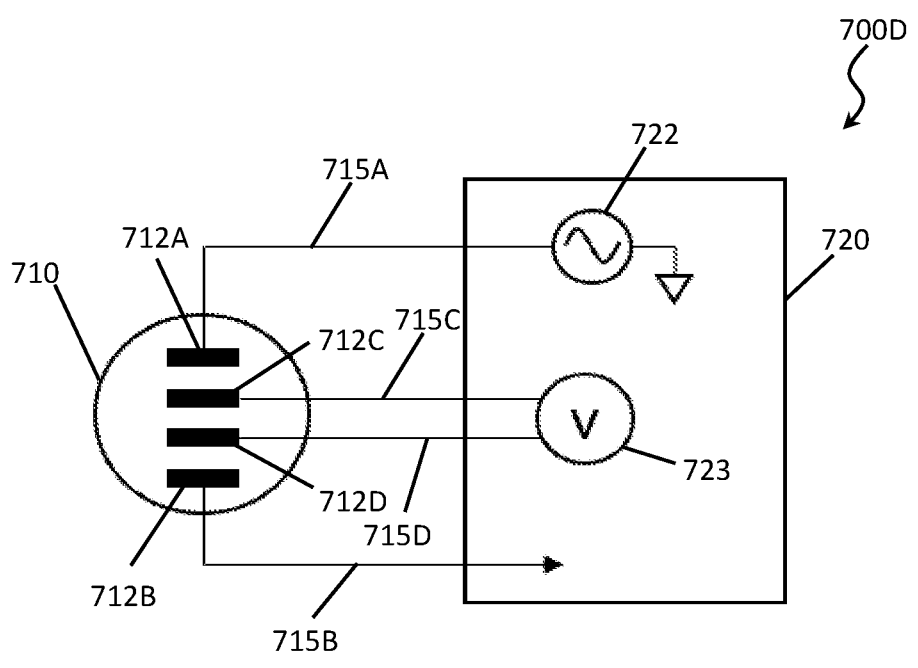

FIG. 11D shows an example of a sweat sensor for measuring a current and/or potential difference between sweat sensing electrodes. The sweat sensor includes four sweat sensing electrodes 712A, 712B, 712C, 712D and an analogue front end module 720 including a signal generator 722 and a voltmeter 723. The first sweat sensing electrode 712A and the second sweat sensing electrode 712B are connected to the signal generator 722 and a ground of the analogue front end 720 in the same way as for the arrangement of FIG. 7A described above. The voltmeter 723 is arranged to measure a potential difference between the third electrode 712C and the fourth electrode 712D; the voltmeter 723 may for example be connected to the third electrode 712C by a third conductive line 715C and the fourth electrode 712D by a fourth conductive line 715D. An electrical parameter of the epidermal sweat may be determined based on the current signal output from the second electrode 712B and the potential difference between the third electrode 712C and fourth electrode 712D.

The sweat sensor of FIG. 11D is a full four point system with four separate electrodes, in which the first electrode 712A acts as a working electrode, the second electrode 712B acts as the counter electrode, the third electrode 712C acts as the working sense electrode and the fourth electrode 712D acts as the reference electrode. In this arrangement, the electrode-electrolyte interface impedance between the electrodes 712A/B/C/D and their respective connecting lines 715A/B/C/D has no influence on the measurement. Therefore, this setup may make more accurate measures of the electrical parameters of the sweat sample.

Figure 12A:
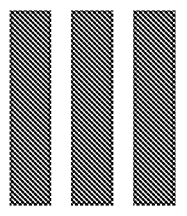
FIGS. 12A to 12F show examples of sweat sensing electrodes according to examples of the present disclosure.
Figure 12B:
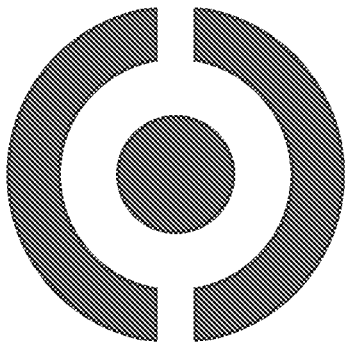
Figure 12C:
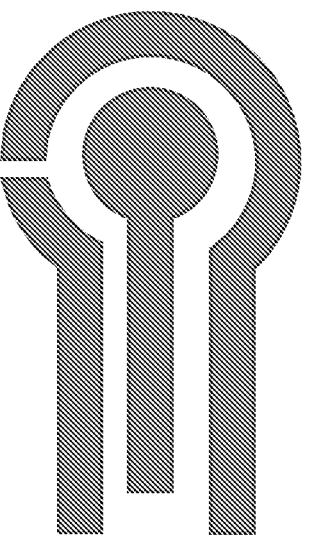
Figure 12D:
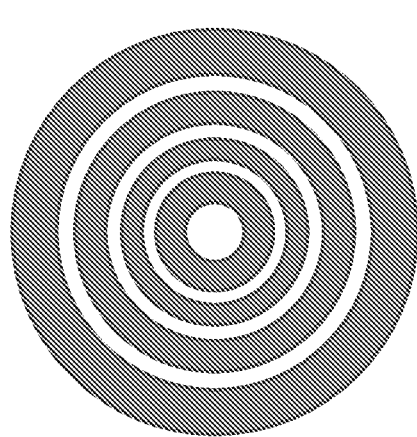
Figure 12E:
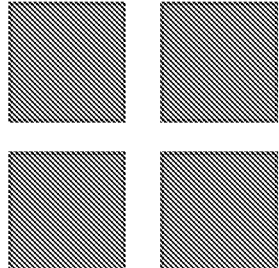
Figure 12F:
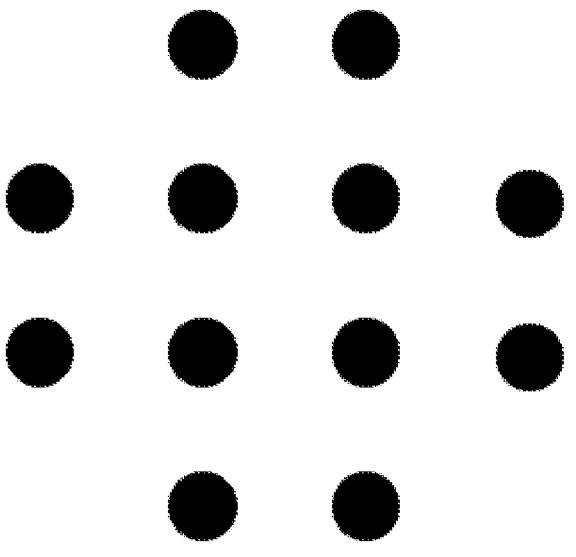

As will be appreciated from the above, depending upon the electrical sweat parameter to be measured and design of the system, there may be one sweat sensing electrode, two sweat sensing electrodes or more than two sweat sensing electrodes. In some examples the sweat sensing electrode is a co-planar electrode, i.e. a structure comprising two or more electrodes in the same plane. By way of example, various co-planar electrode structures are shown in FIGS. 12A-12F, but the present disclosure is not limited thereto. FIGS. 12A-12C have three electrodes, while FIGS. 12D and 12E have four electrodes and FIG. 12F has twelve electrodes. In some examples the sweat sensing electrodes may be inter-digitated electrodes. An interdigitated electrode is an electrode structure in which at least two co-planar electrodes have interlocking parts, such as inter-laced fingers or interlocking spirals. FIGS. 12C and 12D are examples of interdigitated electrodes.

The sweat sensing electrodes may be bare electrodes formed of copper, gold, platinum or another metal or another conductive material such as graphite, or may be electrodes in which the metal or conductive material is coated with a chemical reactant which is to react with the sweat. In some examples each of the electrodes may be formed of the same material, while in other examples each of, or some of, the electrodes may be formed of different materials.

The front end module may output a digital signal to the processor, wherein the digital signal includes a sweat parameter of the sweat as measured by the sweat sensing electrode

17

(s) and front end module. The sweat parameter may be an electrical parameter of the sweat or another parameter which is related to the electrical parameter. For example, the inventor has found that electrical admittance of the sweat is correlated with sweat analyte concentration. Therefore, in some examples, the front-end module may determine a concentration of the sweat analyte based on the measured electrical admittance of the sweat and communicate the sweat analyte concentration to the processor. In other examples, the front end module may communicate the measured electrical admittance of the sweat to the processor and the processor may determine concentration of the sweat analyte based on the measured electrical admittance.

Figure 13:
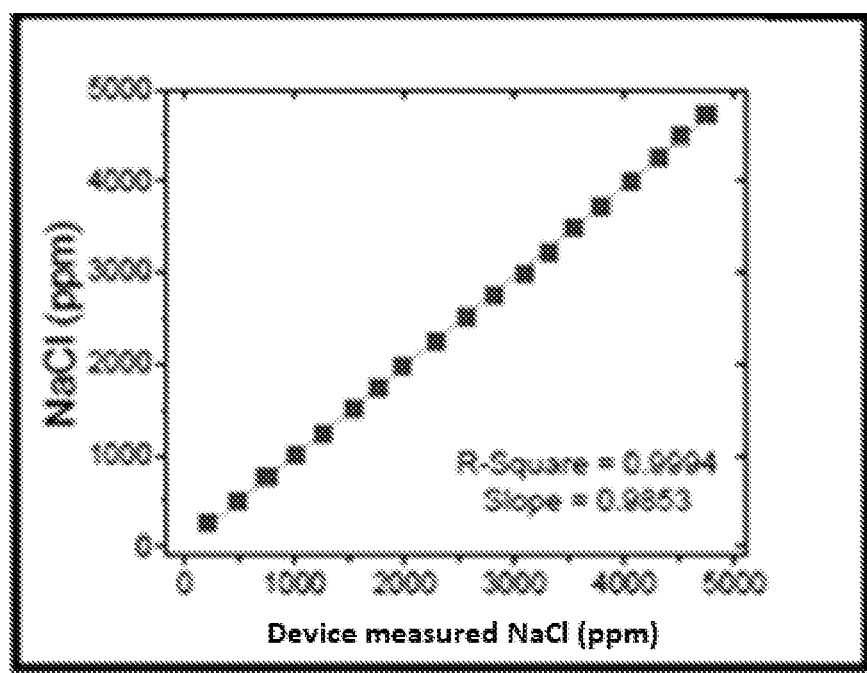
FIG. 13 is a graph showing concentration of a sweat analyte as determined based on admittance of the sweat against the actual concentration of the sweat analyte according to an example of the present disclosure.

FIG. 13 is a graph in which the x-axis represents the NaCl concentration of a solution determined based on the measured admittance of the solution and the y-axis represents the actual NaCl concentration of the solution. As can be seen there was a high level of agreement between the calculated concentration and actual concentration and the relationship was linear within the range of concentrations tested, indicating that the NaCl concentration in the sweat can be determined fairly accurately based on measuring the admittance of the sweat.

Figure 14:
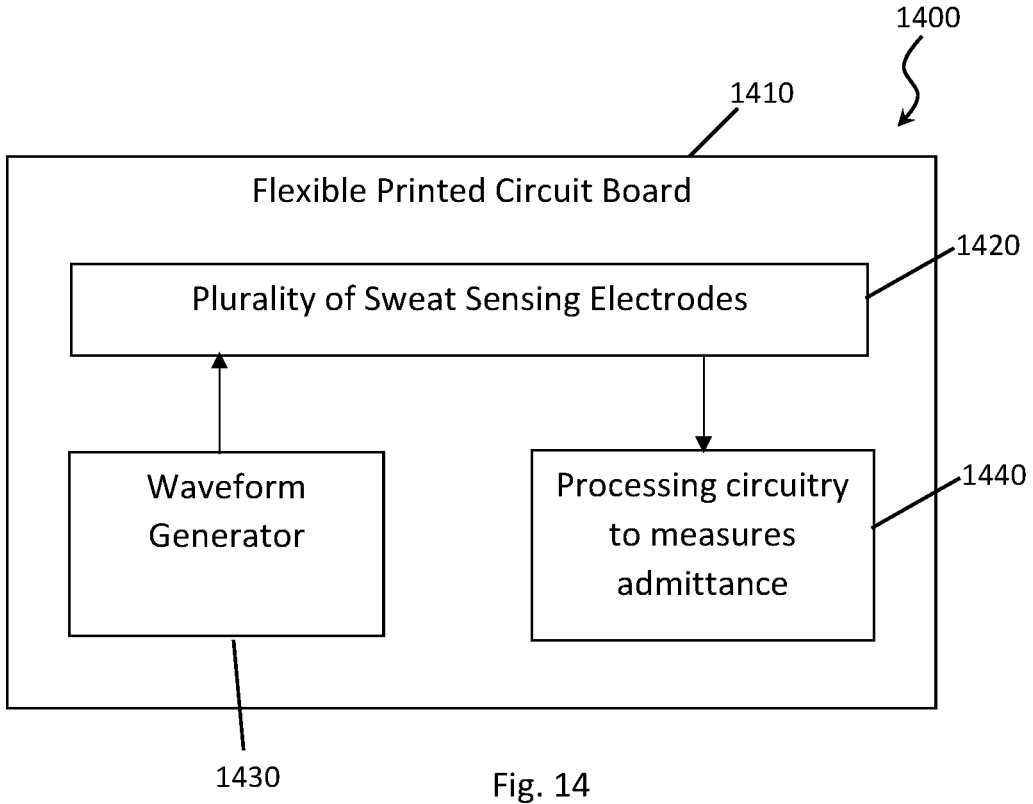
FIG. 14 is a schematic diagram showing one possible structure of a sweat sensor according to an example of the present disclosure.

FIG. 14 is a functional diagram showing an example structure of a sweat sensor 1400 according to an example of the present disclosure which is capable of measuring the admittance of sweat. The sweat sensor includes a printed circuit board 1410, a plurality of sweat sensing electrodes 1420, a waveform generator 1430 and processing circuitry 1440, all of which are mounted to the flexible printed circuit board. The waveform generator 1430 is configured to inject an excitation signal having a frequency to at least one of the sweat sensing electrodes 1420. The processing circuitry 1440 is configured to measure an admittance of sweat between sweat sensing electrodes based on a response of at least one of the plurality of sweat sensing electrodes to the excitation signal. The excitation frequency may for example be in the range 1 mHz-1 MHz. The processing circuitry may comprise a processor, such as a microprocessor, which is configured to determine a concentration of an electrolyte in the sweat based on the measured admittance. As discussed above, admittance has a strong relationship to electrolyte concentration and thus is a relatively reliable indicator of electrolyte concentration. This sweat sensor 1400 may be implemented in a sweat sensor of a heat stress monitor as described in any of the examples above. For instance the plurality of sweat sensing electrodes 1420 may be implemented by the electrode 115, 330, 430, 450, 510 of FIGS. 1, 3, 4B, 4C, 5 and/or the electrodes shown in FIGS. 11A to 11D and 12A to 12D, the waveform generator 1440 may be implemented by a front-end module forming part of the sweat sensor and the processing circuitry 1440 may be implemented by the front-end module and/or by the processor of the heat stress monitor.

In some examples the heat stress monitor may be configured to adjust the sweat parameter based on a temperature sensed by a temperature sensor of the heat stress monitor. This is because temperature may have an effect upon the characteristics of the sweat. For example, sweat analyte concentration may increase with temperature. Accordingly, the processor may compensate the determined sweat parameter to account for differences between the measured temperature and the temperature at which the device was calibrated.

The above embodiments are described by way of example only. Many variations are possible without departing from the scope of the disclosure as defined in the appended claims.

For clarity of explanation, in some instances the present technology has been presented as including individual functional blocks including functional blocks comprising devices, device components, steps or routines in a method embodied in software, or combinations of hardware and software.

Although a variety of examples and other information was used to explain aspects within the scope of the appended claims, no limitation of the claims should be implied based on particular features or arrangements in such examples, as one of ordinary skill would be able to use these examples to derive a wide variety of implementations. Further and although some subject matter may have been described in language specific to examples of structural features and/or method steps, it is to be understood that the subject matter defined in the appended claims is not necessarily limited to these described features or acts. For example, such functionality can be distributed differently or performed in components other than those identified herein. Rather, the described features and steps are disclosed as examples of components of systems and methods within the scope of the appended claims.

It is to be understood that any feature described in relation to any one example may be used alone, or in combination with other features described, and may also be used in combination with any features of any other of the examples, or any combination of any other of the examples.

The invention claimed is:

1. A wearable heat stress monitor comprising:
an analog front end module configured to generate an electrical excitation signal from a waveform generator therein,
a first sensor electrically coupled with the analog front end module, the first sensor comprising a plurality of co-planar electrodes for sensing an admittance of epidermal sweat by detecting said electrical excitation signal generated by the waveform generator and transmitted from a first of the plurality of co-planar electrodes and received by at least another electrode of the plurality of co-planar electrodes, wherein at least one of said electrodes is connected to ground of the analog front end module;
at least one further sensor for sensing a body parameter or an environmental parameter;
a processor to determine a heat stress level by multiplying a sweat analyte concentration determined from the admittance sensed by the first sensor and the body parameter or environmental parameter sensed by the at least one further sensor by a piecewise function,
wherein the piecewise function has a zero value when the admittance is fluctuating and a non-zero value when the admittance is stable, increasing in a non-fluctuating manner or decreasing in a non-fluctuating manner; and
an output module for controlling a user interface element to visually display information of the heat stress level determined by the processor.

2. The heat stress monitor of claim 1 wherein the detected sweat analyte is sodium chloride, a sodium ion or chlorine ion.

3. The heat stress monitor of claim 1 wherein the at least one further sensor comprises a heart rate sensor and a body temperature sensor or an environmental humidity sensor.

4. The heat stress monitor of claim 1 wherein the processor is configured to determine the heat stress level based on normalized values of the sensed admittance, the body parameter and/or the environmental parameter.

5. The heat stress monitor of claim 1 wherein the processor is configured to determine the heat stress level based on applying a respective weighting to each parameter, the weighting applied to the sensed admittance being greater than the weighting(s) applied to the other parameter(s).

6. The heat stress monitor of claim 1 wherein the processor is configured to generate a projected future value of the heat stress level based on heat stress levels determined for previous time periods.

7. The heat stress monitor of claim 6 wherein the processor is configured to generate the projected future value of the heat stress level based on a gradient of the heat stress level over previous time periods.

8. The heat stress monitor of claim 6 wherein the processor is configured to cause the output module to generate an audio or visual alert on the user interface element indicating a risk of dangerous heat stress in response to the projected future value of the heat stress level exceeding a predetermined threshold.

9. The heat stress monitor of claim 7 wherein the processor is configured to cause the output module to generate an audio or visual alert on the user interface element indicating a risk of dangerous heat stress in response to the projected future value of the heat stress level exceeding a predetermined threshold.

10. The heat stress monitor of claim 1 wherein the processor is configured to determine the user is at a heat cramp stage in response to the the sensed admittance being above a first threshold and a heart rate parameter being equal to or above a second threshold.

11. The heat stress monitor of claim 10 wherein the processor is configured to determine that the user is at the heat exhaustion stage in response to determining that the sensed admittance is above a third threshold, while the temperature parameter is equal to or above a fourth threshold, but below a fifth threshold.

12. The heat stress monitor of claim 11 wherein the processor is configured to determine that the user is at the heat stroke stage when subsequent to detecting heat cramp or a heat exhaustion stage, the sensed admittance sensed by the first sensor enters an abnormal range and the body temperature exceeds a sixth threshold.

13. The heat stress monitor of claim 1 wherein the processor is configured to use a machine learning model to determine the heat stress level, a projected future heat stress level and/or a heat stress stage.

14. The heat stress monitor of claim 1 wherein the heat stress monitor comprises a clip for fixing the heat stress monitor to an item of clothing in a position in which the electrode is proximate the skin of the user.

15. The heat stress monitor of claim 1 wherein the first sensor, at least one further sensor, processor and output module are provided on a flexible adhesive patch for attachment to the user's skin.

16. The heat stress monitor of claim 1 wherein the first sensor, at least one further sensor, processor and output module are provided on a band suitable for wearing on a user's limb or forehead and optionally wherein the heat stress monitor is integrated into a smart-watch.

17. The heat stress monitor of claim 1 wherein the processor is determined to detect periods of instability when the sweat parameter is unstable, and disregard sensed admittance values sensed in said periods of instability when determining the heat stress level.

18. The heat stress monitor of claim 17 wherein the processor is configured to detect initial and end stages of sweating based on fluctuations in detected admittance and disregard sensed admittance values sensed in the initial and end stages of sweating when determining the heat stress level.

\* \* \* \* \*